United States Patent [19]

Stenson

[11] 4,236,470
[45] Dec. 2, 1980

[54] PORTABLE STITCHING DEVICE

[76] Inventor: Thomas K. Stenson, 140 Pelham Rd., New Rochelle, N.Y. 10805

[21] Appl. No.: 4,271

[22] Filed: Jan. 17, 1979

[51] Int. Cl.³ .......................................... B65H 54/62
[52] U.S. Cl. .................................. 112/169; 112/171; 128/340
[58] Field of Search ............... 128/340; 112/169, 171, 112/173, 80; 223/104; 28/198

[56] References Cited

U.S. PATENT DOCUMENTS

| | | | |
|---|---|---|---|
| Re. 22,857 | 3/1947 | Ogburn | 128/340 |
| 1,037,864 | 9/1912 | Carlson et al. | 112/169 |
| 1,352,508 | 9/1920 | Ftacek | 112/169 |
| 1,445,348 | 2/1923 | Noble | 128/340 |
| 2,601,564 | 6/1952 | Smith | 112/169 X |
| 4,021,896 | 5/1977 | Stierlein | 112/171 X |

FOREIGN PATENT DOCUMENTS 337579  4/1904  France ...................................... 128/340

*Primary Examiner*—Werner H. Schroeder
*Assistant Examiner*—Andrew M. Falik
*Attorney, Agent, or Firm*—Hopgood, Calimafde, Kalil, Blaustein & Lieberman

[57] ABSTRACT

The invention contemplates a hand-held and hand-operable stitching device capable of performing a stitching operation at substantial offset from the region of manual contact. The stitching is performed as a special filament-carrying needle is shuttled in a reciprocating cycle of alternated release and retention at corresponding needle-retaining ends of two arms having articulated connection remote from their needle-retaining ends.

11 Claims, 7 Drawing Figures

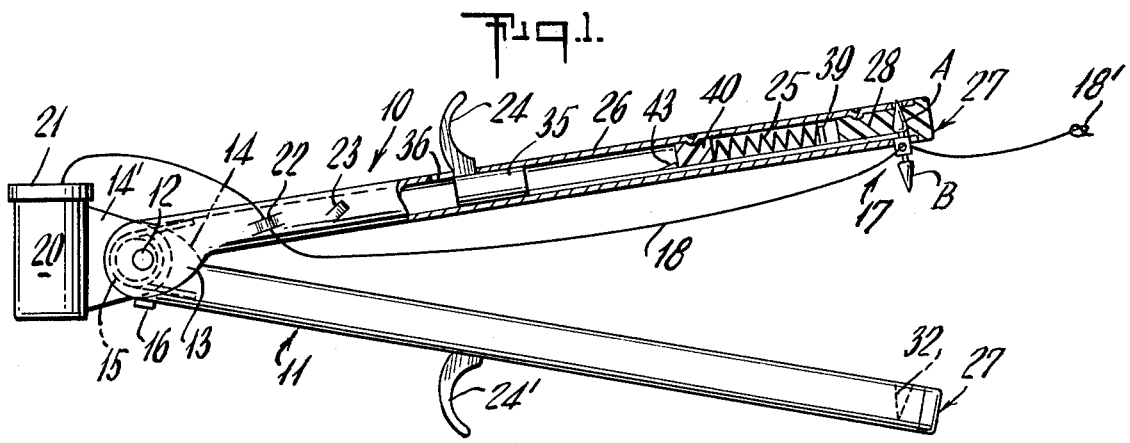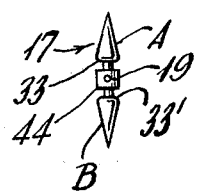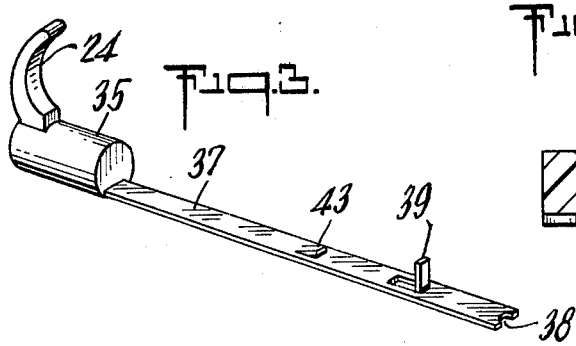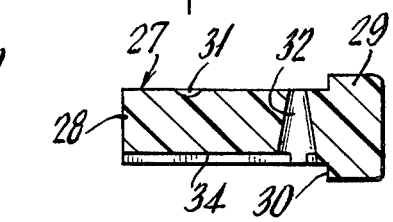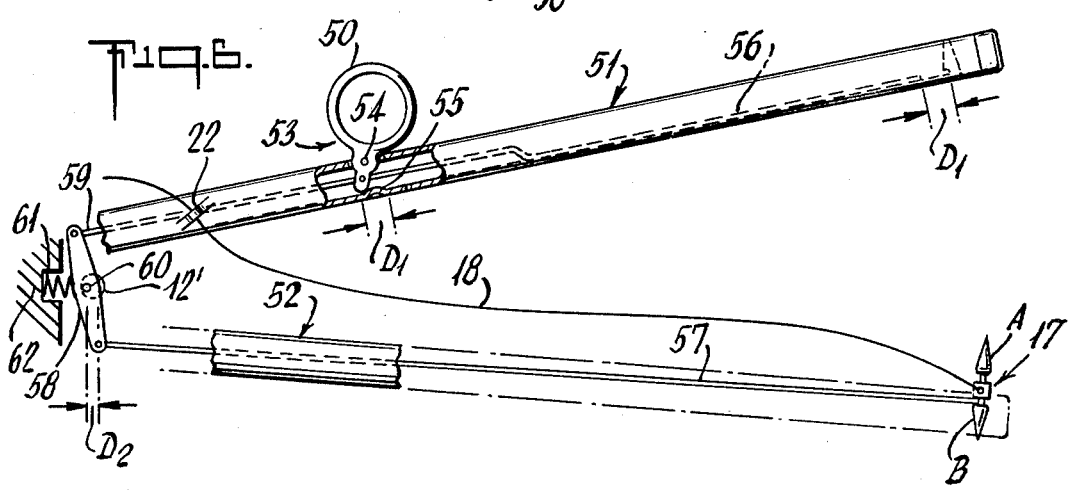

PORTABLE STITCHING DEVICE

This invention relates to portable stitching means which enables simple stitching operations at a location remote from the location of any manual contact.

In the mortuary business, it is important that if the deceased is to be on display, he be prepared for display at best cosmetic advantage. And in these days of increasing numbers of deaths as a result of a disfiguring accident and of increasing instances of disfigurement by reason of postmortem examination, there is an increasing need for funeral-services personnel to perform sufficient stitching and other operations to provide a cosmetically adequate display. To my knowledge, the conventional practice has been to manually perform the requisite stitching, using only a needle and filament, such as a monofilament nylon. Such practice brings the operator in frequent exposure to diseased body matter, with great risk of dangerous personal infection.

It is an object of the invention to provide improved stitching means to substantially reduce the above-noted personal danger associated with current mortuary practice.

A specific object is to provide a hand-held and hand-operated stitching device for the indicated purposes and assuring that the operator can at all times be safely remote from the stitching needle and from the stitching region.

Another specific object is to achieve the above objects with a device which can be operated with simple manual motion, in the nature of pliers or scissors-type actuation.

Another specific object is to meet the above objects with a device which can enable stitching filament to enter the skin at one point and to then leave the skin at a different point, offset from the said one point.

Other objects and various further features of novelty and invention will be pointed out or will occur to those skilled in the art from a reading of the following specification, in conjunction with the accompanying drawings. In said drawings, which show, for illustrative purposes only, preferred embodiments of the invention:

FIG. 1 is a view in side elevation of a stitching device of the invention, partly broken away and in longitudinal section;

FIGS. 2 and 2A are similar views in enlarged elevation of alternative shuttle-needle configurations usable in the device of FIG. 1;

FIG. 3 is a perspective view of actuating structure forming part of the device of FIG. 1;

FIGS. 4 and 5 are similar enlarged views in longitudinal section, for each of two components of the device of FIG. 1; and FIG. 6 is a simplified and somewhat schematic view of a modified stitching device of the invention.

The stitching device of FIG. 1 comprises upper and lower arms 10-11 which are pivotally articulated at a pin 12. The pinned ends of arms 10-11 are locally flattened to define ears 13-14 which are in side-by-side sliding abutment for stable pivoted action, it being preferred that two spaced ears 13 of arm 10 straddle and engage both lesser-spaced ears 14 of arm 11. A preloaded coil spring 15 is captive in the space between ears 14 and is located by passage of pin 12 therethrough, the ends of spring 15 extending tangentially from the coil and bearing upon inner surfaces of arms 10-11 to normally urge arms 10-11 to their open position, shown in FIG. 1. A lug 16 formed out of the material of each ear 13, and bent to intercept further opening movement of adjacent ear 14, provides means to determine the limiting open-arm position shown. Except for their described ear formations 13-14, the arms 10-11 may be generally tubular, as by cylindrically roll-forming the same from sheet-metal stock.

In accordance with the invention, each outwardly projecting end of one of the arms 10-11 is adapted to receive, support and releasably retain a different one of the two needle-pointed ends of a shuttle 17, alternative forms of which are shown in FIGS. 2 and 2A. And a stitching filament 18, as for example a length of monofilament nylon, passing through a central eye 19 between the pointed ends of needle 16 is carried by shuttle action in a succession of cycles of reciprocation from the upper-arm referenced position shown in FIG. 1, to a similar but lower-arm referenced position, and then back to the upper-arm referenced position. As shown, a container 20 with its removably secured cover 21 is carried by a rearward extension 14' of ears 14; a bobbin or spool of filament 18 will be understood to be supported and contained at 20-21, and payed out as needed via a suitable guide loop 22 in arm 10 and thence to the eye 19 of needle 17. A simple cutting lug 23 formed out of arm 10 near guide loop 22 provides means for severing filament 18 remote from needle 17 and the stitching region.

In the form of FIG. 1, a separate finger-actuated release trigger 24 (24') must be drawn back against the action of a preloading spring 25 in order to permit withdrawal of shuttle 17 from one of its two possible retained positions; the finger-actuated mechanism of one arm is a duplicate of that in the other arm and therefore a description for the case of arm 10 will suffice.

The open end of the tubular part 26 of arm 10 is closed by a plug member 27 (FIG. 4), having a shank 28 to fill and securely fit the bore of tube 26 and having an enlarged head 29 which defines a shoulder 30 to seat against the end of tube 26. A local recess 31 in the shank 28 provides key-locking space within which a local inward key may be formed from tube 26 to permanently retain the assembly and angular orientation of plug 27 in tube 26. The shank 28 has a transversely extending socket 32 which is contoured to receive and orient a retained end of needle 17, there being aligned local openings in tube 26 in register with each of the adjacent contour intercepts of socket 32 so that a fully inserted needle can be observed projecting slightly above arm 10. When thus fully inserted, a shoulder 33 beneath the base of the upper end of needle 17 registers with or just clears the elevation of the bottom 34 of an elongate guide groove or channel along the lower region of shank 28; this channel will be understood to angularly position and slidably accommodate releasable needle-retaining means forming part of or connected to the trigger 24.

As best shown in FIG. 3, the release finger or trigger 24 is an injection-molded plastic part having a cylindrical base block 35 which is longitudinally slidable within and guided by the bore of tube 26, with the trigger 24 projecting externally and upward through a local straight slot 36 in tube 26. And the releasable needle-retaining means associated therewith is a metal strip 37 permanently secured at one end to base 35, the other end of strip 37 being preferably locally recessed at 38 to permit needle-retaining engagement under the shoulder 33. A lug 39 struck up from strip 37 receives normally-forward bias force from spring 25, i.e., in the direction to assure a normal needle-retaining capability for strip 37. The other end of spring 25 may be fixedly referenced to arm 10 via a local radially inward and downwardly extending lug struck from tube 26, but in the form shown an additional plug 40 (FIG. 5) of injection-molded plastic serves the purpose. Plug 40 tightly fits the bore of tube 26 and is permanently retained by a local inward key deformation of tube 26 into a key recess 41 of plug 40; as with plug shank 28, a bottom groove or channel 42 in plug 40 accommodates longitudinal sliding action of strip 37. The forward and backward limits of motion of strip 37 may be determined by the limits of freedom of trigger 24, as permitted by the length of slot 36; however, to limit the normal spring-urged forward motion, a short lug 43 is shown struck up from strip 37 for forward-limiting abutment with plug 40.

In the preferred needle 17 of FIGS. 1 and 2, the like but oppositely pointed upper and lower ends A-B are necked down at connection of their shoulders 33-33' to a short central body 44 in which the eye 19 is formed; body 44 is preferably of the maximum or base diameter of each of the ends A-B. A fit of the upper end A to upper arm 10, the taper of the end A has already been described as being located and oriented by the matching concavity of socket 32, and in its spring-urged normal forward position the recess 38 of strip 37 straddles the needle neck between body 44 and end A, beneath shoulder 33; at the same time, it will be understood that an aligned circular opening in tube 26 is sized to receive and stabilize body 44, adjacent and slightly above the eye 19, i.e., so as not to foul the filament 18 at 19. In the needle 17' of FIG. 2A, the necked down region 44' between upper and lower ends A'-B' is elongate and contains a central eye 19', there being no enlarged body as in FIG. 2; thus in FIG. 2A, total reliance is placed on socket 32, for needle stability when retained by arm 10.

In operation, and having first threaded filament 18 through eye 19, and preferably after (1) cutting off (at 23) a more than adequate filament length for the job to be done and (2) knotting the free ends together so as to enable stitching with double strands of filament, the stitching device is manipulated to place the projecting end of arm 11 beneath skin of the region to be stitched, whereupon arms 10-11 are squeezed together, causing the lower needle end B to pierce the skin and enter the socket 32 of arm 11, for latched retention by the strip 37 associated with trigger 24'. At this point, both arms 10-11 are retained close together, being latched to the respective ends A-B of the shuttle needle 17. Retracting finger actuation of the upper-arm trigger 24 releases arm 10 from needle 17, allowing arm 10 to rise above the skin, and allowing the stitching device to be manipulated via arm 11 to bring about full passage of needle 17 and its filament through the pierced skin. Upon laterally displacing arm 11 and its retained needle, the device is again squeezed to cause the upper needle end A to pierce another point in the skin and to enter the socket 32 of arm 10, thus again latching needle 17 to both arms 10-11. Upon actuation of trigger 24', the lower needle end B is released, allowing arm 10 to again rise, this time bringing needle 17 and filament 18 upwardly through the second pierced point of the skin. At this point, the double strand may be pulled through both skin piercings by lifting the stitching device (with needle 17 at arm 10) until the knot seats, at which point the effectiveness of the anchor knot may be tested under a light tension; and it will be understood that, if need be, more than one cycle of shuttle reciprocation may be made between nearby points in the skin to assure adequate skin anchorage at the end of filament 18. Having assured adequate filament anchorage, the next (downward) passage of needle 17 through skin may be made via skin on the other side of the skin cleavage to be sewn, and with succeeding skin passes, alternating on opposite sides of the cleavage, the stitching can be made to effectively "lace" the cleavage, i.e., to draw together both sides of the cleavage. Once the sewing action is complete, i.e., cleavage sides having been drawn together, the operation may be finished by needle shuttling to tie the filament.

The stitching device of FIG. 6 differs from that of FIG. 1, in that a single trigger 50 on the upper one of two pivotally articulated arms 51-52 serves to effect transfer of the needle-retaining function, from arm 51 to arm 52, and back again in the described shuttle sequence. Trigger 50 is shown as a finger-engageable loop or ring at the exposed upper end of a lever 53, pivoted to arm 51 at 54, and having its lower end selectively shiftable to the forward or rear limit of a displacement distance $D_1$. In the process of accomplishing the displacement $D_1$, the lower end of lever 53 rides upon and transiently outwardly displaces a local spring detent lug 55, which may be defined at a U-shaped local piercing of arm 52. A first link 56 connects the lower end of lever 53 to mechanism as described for strip 37 in FIG. 1, i.e., to releasably retain the upper end A of the shuttle needle 17, and in FIG. 6 link 56 is shown retracted for the forward position of trigger 50. A second link 57 is similarly movable within the lower arm 52 and is connected to the lower end of lever 53 via a rocker arm 58 and a further link 59, within arm 51.

The pivotal suspension of rocker arm 58 may be at the pivotal connection of arms 51-52 or slightly offset therefrom; for this reason FIG. 6 does not show the pivoted connection of arms 51-52. However, it is important that a degree of resiliently loaded lost motion be incorporated in the connection of lever 53 to the releasable-retaining means (link 57) in lower arm 52; such lost motion is denoted $D_2$ in FIG. 6 and should be small enough compared to $D_1$ so as to permit lever 53 to do its control-shifting job, while allowing the loaded lost motion to compensate for the effective angularity displacement of the rocker arm 58 by reason of operating arms 51-52 in their squeezing cycle of reciprocation. Thus, for the case in which rocker arm 58 is to pivot substantially on the axis of pivotal connection of arms 51-52, the pivot pin (analogous to pin 12 in FIG. 1) may be a hollow tube having a bore contour suggested at 12' in FIG. 6. Within this bore 12', a rocker-arm pivot pin 60 of relatively small diameter has freedom for movement, to the extent $D_2$, and preloading spring means 61, referenced at 62 to the pinned ear end of one of arms 51-52, normally urges the rocker-arm pivot pin 60 in the direction of the projecting ends of arms 51-52. In the needle-latching position shown in FIG. 6 for means 57 in the lower arm 52, a squeezing displacement of arms 51-52 would be accompanied by a $D_2$ retraction of means 57 if pivot pin 60 provided a fixed axis of rocker-arm action; however, since the described resiliently loaded lost motion is available, the needle-retaining position of means 57 is held for the full squeezing displacement of arms 51-52, it being noted that the detent-retention resistance (at 55) against displacement of trigger 50 is of magnitude to cause all necessary lost-motion displacement of the loading spring 61.

In operation of the stitching device of FIG. 6, the trigger 50 is shifted only when both arms 51-52 are squeezed together, assuring nested location of both needle ends A-B in the sockets 32 of the respective arms 51-52. Such shifting, from the trigger-forward position of FIG. 6 to the trigger-retracted position, will place the means 56 in engaged relation beneath shoulder 33 of the needle end A, while retracting the means 57 clear of any such relation with the shoulder 33' of needle end B. Release of arms 51-52 then draws needle 17 and the filament in an upward shuttle displacement with arm 51. On the next squeezing together of arms 51-52, trigger 50 should be shifted again to its forward position, causing simultaneous release of the needle from arm 51 and its re-engagement to arm 52.

The described invention will be seen to achieve all stated objects with simple structure which is readily manipulated and actuated and which at the same time assures that the operator can keep himself safely remote from the region which he is stitching. The operator is not limited to the style of stitching which has been specifically described, in that the device of the invention essentially is a remote needle-handling device which leaves stitching style almost entirely up to the operator; thus, for example, by making the first stitching pass outwardly from beneath the skin, the initial anchor knot may be "buried" and therefore not externally visible.

While the invention has been described for preferred forms shown, it will be understood that modifications may be made without departing from the scope of the invention.

What is claimed is:

1. A manually operable portable stitching device, comprising two arms projecting from a location of articulating connection of said arms at a given angle therebetween in an unsqueezed open position, a shuttle needle having a central eye for passage of filament and pointed at its longitudinal ends, said needle having first and second peripheral shoulders near but on opposite sides of said eye, said arms each having a needle-receiving opening adapted to accommodate one of the pointed ends of said needle, said needle-receiving openings being at corresponding locations in the respective projecting ends of said arms, the orientation of said openings being such that when one end of the needle is carried at one of said openings its other end is aligned for insertion into and reception in the other of said openings upon articulated movement of said arms into a contiguous relationship with each other in a squeezed closed position, said device further including releasable needle-retaining means at each opening for selective retention and release of the needle when a needle end is received in the opening, each of said arms including a latch means releasably biased by a spring means into engagement with the adjacent shoulder of a needle end, and each of said arms further including a selectively operable release mechanism for the latch of the involved arm, and manually operable actuating means associated with said release mechanisms and selectively operable in both said open and closed arm positions for moving said latch means away from said needle shoulder so that said needle end is released from said opening.

2. The stitching device of claim 1, in which said last-defined means comprises a first actuator carried by one of said arms and connected for selective manual operation of the release mechanism associated with said one arm, and a second actuator similarly connected and carried by the other of said arms for selective manual operation of the release mechanism associated with said other arm.

3. The stitching device of claim 1, in which said last-defined means comprises a single actuator carried by one of said arms and selectively actuable between first and second positions, said actuator being so connected to both said release mechanisms as in its first position to determine the latch-release function of one of said release mechanisms while also determining the needle-retaining function of the other of said release mechanisms, and in said second position to determine the needle-retaining function of said one release mechanism while also determining the latch-release function of the other of said release mechanisms.

4. The stitching device of claim 3, in which said single actuator comprises a pivoted lever one end of which projects externally of said one arm for manual actuation between forward and backward limits of its movement, the other end of said lever being movable longitudinally within said one arm in accordance with said movement and being connected to the respective releasable mechanisms.

5. The stitching device of claim 4, in which the connections of sid lever to said respective release mechanisms are via relatively rigid linkages.

6. The stitching device of claim 1, in which one of said arms includes supporting means adapted to hold a supply of filament material to be stitched.

7. The stitching device of claim 6, in which one of said arms includes a filament guide between the longitudinal location of said supporting means and the longitudinal locations of said needle-receiving openings.

8. The stitching device of claim 7, in which one of said arms includes filament-cutting means between the longitudinal location of said supporting means and the longitudinal location of said needle-receiving openings.

9. A manually operable portable stitching device, comprising two arms projecting from a location of articulating connection of said arms, a shuttle needle having a central eye for passage of filament and pointed at its longitudinal ends, said arms each having a needle-receiving opening adapted to accommodate one of the pointed ends of said needle, said needle-receiving openings being at corresponding locations in the respective projecting ends of said arms, the orientation of said openings being such that when one end of the needle is carried at one of said openings its other end is aligned for insertion into and reception in the other of said openings upon articulated approach of said arms to each other, said device further including releasable needle-retaining means at each opening for selective retention and release of the needle when a needle end is received in the opening, and actuating means carried by said device for alternating the needle-retaining and needle-releasing function of one releasable means in interlace with the needle-releasing and needle-retaining function of the other releasable means, said actuating means comprising a single actuator carried by one of said arms and selectively actuable between first and second positions, said actuator being so connected to both said releasable means as in its first position to determine the needle-release function of one of said releasable means while also determining the needle-retaining function of the other of said releasable means, and in said second position to determine the needle-retaining function of said one releasable means while also determining the needle-releasing function of the other of said releasable means, said single actuator comprising a pivoted lever one end of which projects externally of said one arm for manual actuation between forward and backward limits of its movement, the other end of said lever being movable longitudinally within said one arm in accordance with said movement and relatively rigid linkages connecting the same to the respective releasable means, the linkage connection of said lever to the releasable means of said other arm including a rocker arm pivotally mounted in the vicinity of the articulating connection of said arms.

10. The stitching device of claim 9, in which said linkage connection of said lever to the releasable means of said other arm includes a spring-biased lost-motion connection, the spring-bias direction being in the needle-engaging direction of the releasable means associated with sid other arm, the effective extent of such lost motion being substantially less than the extent of linkage displacement when said lever is shifted from one to the other of its forward and backward positions.

11. A manually operable portable stitching device, comprising two arms projecting from a location of articulating connection of said arms, a shuttle needle having a central eye for passage of filament and pointed at its longitudinal ends, said arms eacgh having a needle-receiving opening adapted to accommodate one of the pointed ends of said needle, said needle-receiving opening being at corresponding locations in the respective projecting ends of said arms, the orientation of said openings being such that when one end of the needle is carried at one of said openings its other end is aligned for insertion into and reception in the other of said openings upon articulated approach of said arms to each other, said device further including releasable needle-retaining means at each opening for selective retention and release of the needle when a needle end is received in the opening, and actuating means carried by said device for alternating the needle-retaining and needle-releasing function of one releasable means in interlace with the needle-releasing and needle-retaining function of the other releasable means, said last-defined means comprising a single actuator carried by one of said arms and selectively actuable between first and second positions, said actuator being so connected to both said releasable means as in its first position to determine the needle-release function of one of said releasable means while also determining the needle-retaining function of the other of said releasable means, and in said second position to determine the needle-retaining function of said one releasable means while also determining the needle-releasing function of the other of said releasable means, said single actuator comprising a pivoted lever one end of which projects externally of said one arm for manual actuation between forward and backward limits of its movement, the other end of said lever being movable longitudinally within said one arm in accordance with said movement and being connected to the respective releasable means, and resiliently yieldable means associated with said lever and said one arm yieldably retaining said lever in each of its shiftable positions.

* * * * *